United States Patent
Smith et al.

(10) Patent No.: US 10,603,067 B2
(45) Date of Patent: Mar. 31, 2020

(54) POLYPECTOMY SNARE DEVICES

(71) Applicant: BOSTON SCIENTIFIC SCIMED, INC., Maple Grove, MN (US)

(72) Inventors: Paul Smith, Smithfield, RI (US); Samuel Raybin, Marlborough, MA (US); Kevin J. McElwee, Acton, MA (US); Brian Gaffney, Rutland, MA (US); Naroun Soun, Lawrence, MA (US); Ismail Guler, Maple Grove, MN (US); Brian J. Hanson, Shoreview, MN (US); Elias A. Khoury, Maple Grove, MN (US); Steven R. Larsen, Lino Lakes, MN (US); Daniel H. VanCamp, Elk River, MN (US); Wade R. Strelow, Maple Grove, MN (US); Ryan Wales, Northborough, MA (US); Robert B. DeVries, Northborough, MA (US); Peter J. Shank, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 244 days.

(21) Appl. No.: 15/663,568

(22) Filed: Jul. 28, 2017

(65) Prior Publication Data
US 2018/0028220 A1 Feb. 1, 2018

Related U.S. Application Data

(60) Provisional application No. 62/367,902, filed on Jul. 28, 2016.

(51) Int. Cl.
*A61B 17/3205* (2006.01)
*A61B 18/14* (2006.01)
(Continued)

(52) U.S. Cl.
CPC .... *A61B 17/32056* (2013.01); *A61B 18/1485* (2013.01); *A61B 2017/00309* (2013.01);
(Continued)

(58) Field of Classification Search
CPC ............ A61B 17/32056; A61B 17/211; A61B 2017/2212; A61B 2017/00526; A61B 2018/141
See application file for complete search history.

(56) References Cited

U.S. PATENT DOCUMENTS

| 1,127,948 A | 2/1915 | Wappler |
| 2,036,528 A | 4/1936 | Kesling |

(Continued)

FOREIGN PATENT DOCUMENTS

| DE | 2829159 A1 | 1/1980 |
| DE | 3616193 A1 | 11/1986 |

(Continued)

*Primary Examiner* — Katherine M Rodjom
(74) *Attorney, Agent, or Firm* — Seager, Tufte & Wickhem, LLP

(57) ABSTRACT

Polypectomy devices and methods for making and using polypectomy devices are disclosed. An example polypectomy device may include an elongate sheath having a proximal end region and a distal end region. A shaft may be slidably disposed within the sheath. A handle may be coupled to the proximal end region of the sheath. The handle may be designed to axially shift the shaft relative to the sheath. A snare may be coupled to the shaft. The snare may include a first region, a traction region, and a distal tip region. The first region may have a non-circular cross-sectional shape. The traction region may include a plurality of traction members. At a position between two adjacent traction members the snare may have a reduced cross-sectional area relative to the first region. The distal tip region may have a circular cross-sectional shape.

20 Claims, 14 Drawing Sheets

(51) Int. Cl.
  *A61B 17/32* (2006.01)
  *A61B 17/00* (2006.01)
  *A61B 18/00* (2006.01)

(52) U.S. Cl.
  CPC .............. *A61B 2017/00323* (2013.01); *A61B 2017/00526* (2013.01); *A61B 2017/00862* (2013.01); *A61B 2017/00867* (2013.01); *A61B 2017/320064* (2013.01); *A61B 2018/00595* (2013.01); *A61B 2018/141* (2013.01)

(56) References Cited

U.S. PATENT DOCUMENTS

| | | | |
|---|---|---|---|
| 2,950,609 A | 8/1960 | Goodloe |
| 3,554,192 A | 1/1971 | Isberner |
| 3,805,791 A | 4/1974 | Seuberth et al. |
| 3,895,636 A | 7/1975 | Schmidt |
| 3,910,279 A | 10/1975 | Okada et al. |
| 3,955,578 A | 5/1976 | Chamness et al. |
| 4,256,113 A | 3/1981 | Chamness |
| 4,294,254 A | 10/1981 | Chamness |
| 4,326,530 A | 4/1982 | Fleury, Jr. |
| 4,327,711 A | 5/1982 | Takagi |
| 4,345,599 A | 8/1982 | McCarrell |
| 4,430,083 A | 2/1984 | Ganz et al. |
| 4,493,320 A | 1/1985 | Treat |
| 4,503,855 A | 3/1985 | Maslanka |
| 4,590,938 A | 5/1986 | Segura et al. |
| 4,593,680 A | 6/1986 | Kubokawa |
| 4,619,260 A | 10/1986 | Magill et al. |
| 4,632,110 A | 12/1986 | Sanagi |
| 4,706,656 A | 11/1987 | Kuboto |
| 4,763,668 A | 8/1988 | Macek et al. |
| 4,785,825 A | 11/1988 | Romaniuk et al. |
| 4,790,831 A | 12/1988 | Skribiski |
| D301,614 S | 6/1989 | Kozak et al. |
| 4,840,176 A | 6/1989 | Ohno |
| 4,840,623 A | 6/1989 | Quackenbush |
| 4,869,238 A | 9/1989 | Opie et al. |
| 4,872,456 A | 10/1989 | Hasson |
| 4,905,691 A | 3/1990 | Rydell |
| 4,945,920 A | 8/1990 | Clossick |
| 4,950,232 A | 8/1990 | Ruzicka et al. |
| 4,967,732 A | 11/1990 | Inoue |
| 4,973,321 A | 11/1990 | Michelson |
| 5,005,755 A | 4/1991 | Takahashi et al. |
| 5,026,371 A | 6/1991 | Rydell et al. |
| 5,059,199 A | 10/1991 | Okada et al. |
| 5,066,295 A | 11/1991 | Kozak et al. |
| 5,084,054 A | 1/1992 | Bencini et al. |
| 5,114,403 A | 5/1992 | Clarke et al. |
| 5,125,909 A | 6/1992 | Heimberger |
| 5,129,913 A | 7/1992 | Ruppert |
| 5,147,316 A | 9/1992 | Castillenti |
| 5,147,373 A | 9/1992 | Ferzli |
| RE34,110 E | 10/1992 | Opie et al. |
| 5,156,590 A | 10/1992 | Vilmar |
| 5,158,561 A | 10/1992 | Rydell et al. |
| 5,163,942 A | 11/1992 | Rydell |
| 5,176,677 A | 1/1993 | Wuchinich |
| 5,176,702 A | 1/1993 | Bales et al. |
| 5,179,935 A | 1/1993 | Miyagi |
| 5,183,470 A | 2/1993 | Wettermann |
| 5,201,740 A | 4/1993 | Nakao et al. |
| 5,201,743 A | 4/1993 | Haber et al. |
| 5,244,619 A | 9/1993 | Burnham |
| 5,254,117 A | 10/1993 | Rigby et al. |
| 5,254,130 A | 10/1993 | Poncet et al. |
| 5,279,280 A | 1/1994 | Bacich et al. |
| 5,281,220 A | 1/1994 | Blake, III |
| 5,281,230 A | 1/1994 | Heidmueller |
| 5,290,294 A | 3/1994 | Cox et al. |
| 5,318,564 A | 6/1994 | Eggers |
| 5,334,169 A | 8/1994 | Brown et al. |
| 5,336,227 A | 8/1994 | Nakao et al. |
| 5,358,493 A | 10/1994 | Schweich, Jr. et al. |
| 5,376,094 A | 12/1994 | Kline |
| 5,403,342 A | 4/1995 | Tovey et al. |
| 5,404,887 A | 4/1995 | Prather |
| 5,406,939 A | 4/1995 | Bala |
| 5,439,478 A | 8/1995 | Palmer |
| 5,465,710 A | 11/1995 | Miyagi et al. |
| 5,486,182 A | 1/1996 | Nakao et al. |
| 5,496,292 A | 3/1996 | Burnham |
| 5,501,692 A | 3/1996 | Riza |
| 5,542,948 A | 8/1996 | Weaver et al. |
| 5,584,843 A | 12/1996 | Wulfman et al. |
| 5,588,964 A | 12/1996 | Imran et al. |
| 5,591,202 A | 1/1997 | Slater et al. |
| 5,601,533 A | 2/1997 | Hancke et al. |
| 5,647,846 A | 7/1997 | Berg et al. |
| 5,681,296 A | 10/1997 | Ishida |
| 5,718,360 A | 2/1998 | Green et al. |
| 5,741,271 A | 4/1998 | Nakao et al. |
| 5,746,747 A | 5/1998 | McKeating |
| 5,755,724 A | 5/1998 | Yoon |
| 5,759,187 A | 6/1998 | Nakao et al. |
| 5,762,631 A | 6/1998 | Klein |
| 5,766,217 A | 6/1998 | Christy |
| 5,769,841 A | 6/1998 | Odell et al. |
| 5,792,116 A | 8/1998 | Berg et al. |
| 5,800,444 A | 9/1998 | Ridinger et al. |
| 5,814,052 A | 9/1998 | Nakao et al. |
| 5,817,111 A | 10/1998 | Riza |
| 5,820,464 A | 10/1998 | Parlato |
| 5,827,177 A | 10/1998 | Oneda et al. |
| 5,827,272 A | 10/1998 | Breining et al. |
| 5,846,248 A | 12/1998 | Chu et al. |
| 5,860,975 A | 1/1999 | Goble et al. |
| 5,882,347 A | 3/1999 | Mouris-Laan et al. |
| 5,885,508 A | 3/1999 | Ishida |
| 5,906,620 A | 5/1999 | Nakao et al. |
| 5,906,621 A | 5/1999 | Secrest et al. |
| 5,957,932 A | 9/1999 | Bates et al. |
| 5,961,511 A | 10/1999 | Mortier et al. |
| 5,971,994 A | 10/1999 | Fritzsch |
| 5,984,904 A | 11/1999 | Steen et al. |
| 5,984,920 A | 11/1999 | Steinbach |
| 5,989,247 A | 11/1999 | Chambers |
| 5,993,474 A | 11/1999 | Ouchi |
| 6,001,096 A | 12/1999 | Bissinger et al. |
| 6,010,512 A | 1/2000 | Chu et al. |
| 6,015,381 A | 1/2000 | Ouchi |
| 6,015,415 A | 1/2000 | Avellanet |
| 6,024,708 A | 2/2000 | Bales et al. |
| 6,027,460 A | 2/2000 | Shturman |
| 6,050,995 A | 4/2000 | Durgin |
| 6,068,603 A | 5/2000 | Suzuki |
| 6,071,233 A | 6/2000 | Ishikawa et al. |
| 6,074,408 A | 6/2000 | Freeman |
| 6,090,073 A | 7/2000 | Gill |
| 6,090,129 A | 7/2000 | Ouchi |
| 6,093,195 A | 7/2000 | Ouchi |
| 6,117,141 A | 9/2000 | Ouchi |
| 6,183,482 B1* | 2/2001 | Bates ................... A61B 17/221 606/113 |
| 6,235,026 B1 | 5/2001 | Smith |
| 6,299,612 B1 | 10/2001 | Ouchi |
| 6,409,727 B1 | 6/2002 | Bales et al. |
| 6,454,702 B1 | 9/2002 | Smith |
| 6,517,539 B1 | 2/2003 | Smith et al. |
| 6,761,717 B2 | 7/2004 | Bales et al. |
| 6,773,432 B1 | 8/2004 | Clayman et al. |
| 6,840,900 B2 | 1/2005 | Smith |
| 6,881,186 B2 | 4/2005 | Smith |
| 6,972,007 B2 | 12/2005 | Geiser et al. |
| 9,101,383 B1 | 8/2015 | Dostal et al. |
| 2014/0276911 A1* | 9/2014 | Smith ................... A61B 17/221 606/113 |
| 2015/0105789 A1* | 4/2015 | Raybin ............ A61B 17/32056 606/113 |

(56) References Cited

U.S. PATENT DOCUMENTS

FOREIGN PATENT DOCUMENTS

| | | |
|---|---|---|
| DE | 19953359 A1 | 5/2000 |
| WO | 9222254 A1 | 12/1992 |
| WO | 0042926 A1 | 7/2000 |
| WO | 0053107 A1 | 9/2000 |
| WO | 0110321 A1 | 2/2001 |
| WO | 2005087119 A1 | 9/2005 |

\* cited by examiner

POLYPECTOMY SNARE DEVICES

CROSS-REFERENCE TO RELATED APPLICATIONS

This application claims priority under 35 U.S.C. § 119 to U.S. Provisional Application Ser. No. 62/367,902, filed Jul. 28, 2016, the entirety of which is incorporated herein by reference.

TECHNICAL FIELD

The present disclosure pertains to medical devices, and methods for manufacturing medical devices. More particularly, the present disclosure pertains to polypectomy devices including an end effector.

BACKGROUND

A wide variety of intracorporeal medical devices have been developed for medical use. Some of these devices include guidewires, catheters, endoscopic devices, biopsy devices, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A polypectomy device is disclosed. The polypectomy device, comprises: an elongate sheath having a proximal end region and a distal end region; a shaft slidably disposed within the sheath; a handle coupled to the proximal end region of the sheath, the handle being designed to axially shift the shaft relative to the sheath; a snare coupled to the shaft, the snare including a first region, a traction region, and a distal tip region; wherein the first region has a non-circular cross-sectional shape; wherein the traction region includes a plurality of traction members; wherein at a position between two adjacent traction members the snare has a reduced cross-sectional area relative to the first region; and wherein the distal tip region has a circular cross-sectional shape.

Alternatively or additionally to any of the embodiments above, the snare is formed from a monofilament wire.

Alternatively or additionally to any of the embodiments above, the non-circular cross-sectional shape of the first region is D-shaped.

Alternatively or additionally to any of the embodiments above, the snare has a first leg and a second leg, and wherein the non-circular cross-sectional shape of the first region is D-shaped along both the first leg and the second leg.

Alternatively or additionally to any of the embodiments above, along the first region the first leg and the second leg are designed to be arranged so that planar sides of the first leg and the second leg are positioned adjacent to one another.

Alternatively or additionally to any of the embodiments above, the non-circular cross-sectional shape of the first region is formed by grinding a wire having a round cross-sectional shape.

Alternatively or additionally to any of the embodiments above, at least some of the traction members have a first side having a rounded outer profile and a second side having a planar outer profile.

Alternatively or additionally to any of the embodiments above, all of the plurality of traction members have geometrically congruent cross-sectional shapes.

Alternatively or additionally to any of the embodiments above, at least some of the plurality of traction members have geometrically similar cross-sectional shapes.

Alternatively or additionally to any of the embodiments above, the plurality of traction members are formed by a plurality of annular grooves formed along the snare.

Alternatively or additionally to any of the embodiments above, the plurality of traction members are formed by a helical groove formed along the snare.

Alternatively or additionally to any of the embodiments above, the helical groove varies in depth, pitch, or both along the length of the snare.

Alternatively or additionally to any of the embodiments above, the plurality of traction members are formed by a helical member disposed along the snare.

Alternatively or additionally to any of the embodiments above, the snare is formed from a tubular wire and wherein the plurality of traction members are defined by a plurality of apertures formed through a side wall of the tubular wire.

A polypectomy device is disclosed. The polypectomy device comprises: an elongate sheath; a shaft slidably disposed within the sheath; a monofilament snare wire coupled to the shaft, the snare wire having a first end region, a first loop region, a first traction region, a first distal region, a nipple region, a second distal region, a second traction region, a second loop region, and a second end region; wherein the first end region, the second end region, or both have a non-circular cross-sectional shape; wherein the first traction region, the second traction region, or both include a plurality of traction members; wherein the first distal region has a first reduced cross-sectional area relative to the first end region; wherein the second distal region has a second reduced cross-sectional area relative to the second end region; and wherein at least one of the first distal region, the nipple region, and the second distal region has a circular cross-sectional shape.

Alternatively or additionally to any of the embodiments above, the non-circular cross-sectional shape of the first end region, the second end region, or both is D-shaped.

Alternatively or additionally to any of the embodiments above, at least some of the traction members have a first side with a rounded outer profile and a second side with a planar outer profile.

A method for manufacturing a polypectomy device is disclosed. The method comprises: machining a monofilament wire to form a snare wire, the snare wire having a first end region, a first loop region, a first traction region, a first distal region, a nipple region, a second distal region, a second traction region, a second loop region, and a second end region; wherein the first end region, the second end region, or both have a non-circular cross-sectional shape; wherein the first traction region, the second traction region, or both include a plurality of traction members; wherein the first distal region has a first reduced cross-sectional area relative to the first end region; wherein second distal region has a second reduced cross-sectional area relative to the second end region; wherein at least one of the first distal region, the nipple region, and the second distal region has a circular cross-sectional shape; attaching the first end region and the second end region to an elongate shaft; and disposing the elongate shaft within a sheath.

Alternatively or additionally to any of the embodiments above, the non-circular cross-sectional shape of the first end region, the second end region, or both is D-shaped.

Alternatively or additionally to any of the embodiments above, at least some of the traction members have a first side with a rounded outer profile and a second side with a planar outer profile.

A method for cutting a lesion is disclosed. The method comprises: disposing a snare about a lesion, the snare having a plurality of traction members; engaging the lesion with the traction members; retraction at least a portion of the snare into a sheath; and cutting the lesion by applying electrosurgical energy to the snare.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
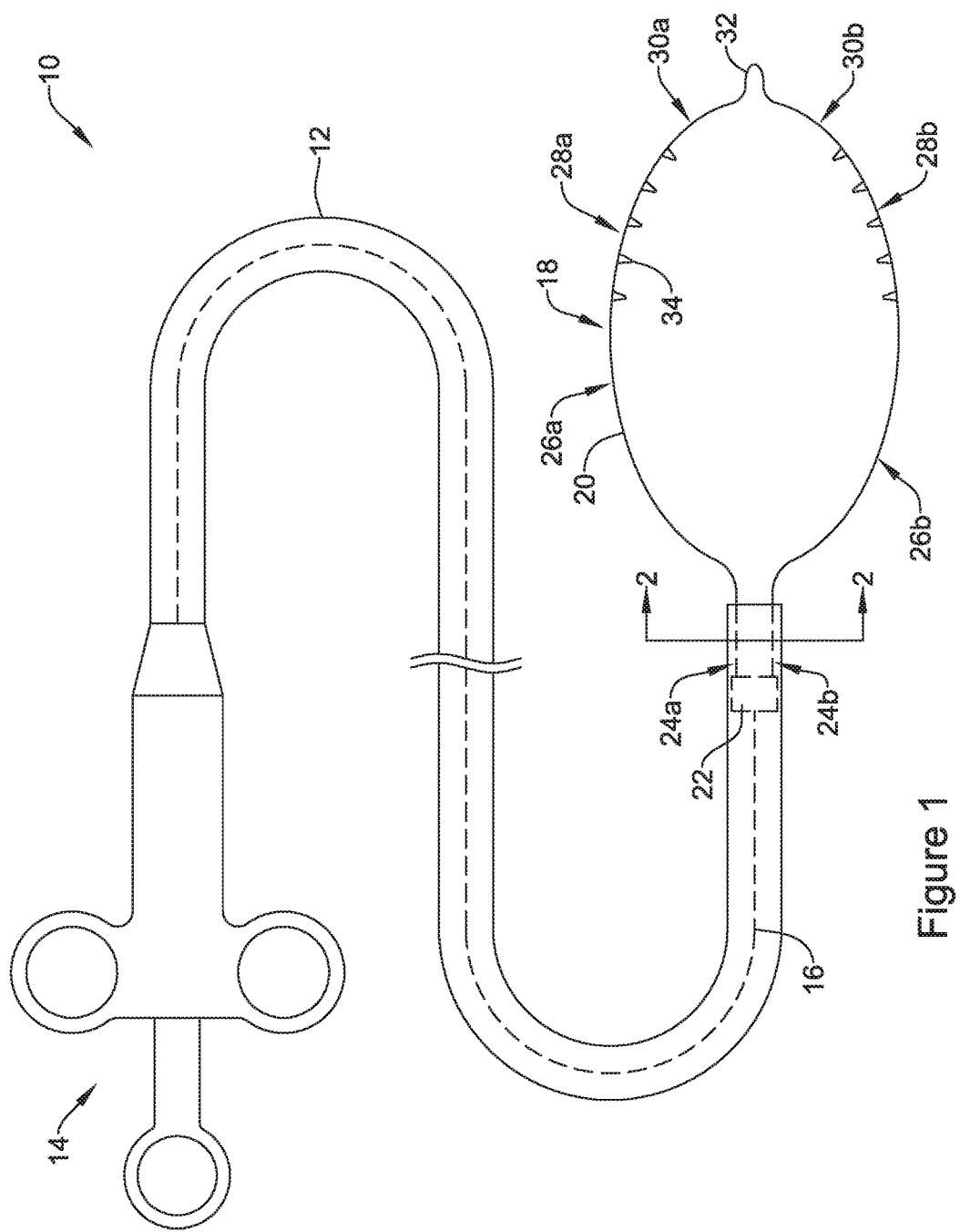
FIG. 1 is a side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Colonic polypectomy generally corresponds to the removal of colorectal polyps, for example, in order to prevent them from turning cancerous. Some polypectomy systems may include a snare that is engaged with a polyp. The polyp may be severed with the snare. For a number of reasons, it may be desirable to reduce buckling of the snare, reduced bending or flipping out of plane, and/or crossing of the legs of the snare. Disclosed herein are polypectomy devices that may include a snare. The snare is designed to have reduced buckling, reduced bending or flipping out of plane, and/or reduced crossing of the snare legs. Some of these and other features are disclosed herein.

FIG. 1 illustrates an example polypectomy device 10. Device 10 may include a sheath 12. A handle 14 may be coupled to sheath 12. Sheath 12 and handle 14 may have a variety of different forms and/or configurations. For example, sheath 12 may have a length that is suitable to extend through an endoscope to a position within a body lumen. This may include a body lumen along the digestive tract such as along the small intestine and/or colon. Other body lumens may also be accessed with sheath 12. A shaft 16 may be slidably disposed within sheath 12. A snare 18 may be coupled to shaft 16. Snare 18 may generally be designed to engage a body tissue such as a polyp and can be used to grab, sever, and/or remove polyps. In some instances, shaft 16 may include an electrical connector so that electrical current (e.g., cautery current) can be applied to snare 18.

Snare 18 may be formed from or otherwise include a wire 20. In at least some instances, wire 20 is a monofilament wire. For the purposes of this disclosure, a monofilament wire is understood to be a wire formed from a single filament and/or a single monolith of material (e.g., a singular polymer, a combination or blend of polymers formed into a single filament/monolith of material, a singular metal or metal alloy (e.g., a nickel-titanium alloy), a combination of metals and/or alloys formed into a single filament/monolith of material, etc.). In other instances, wire 20 may be formed from a plurality of filaments such as a plurality of braided filaments. Wire 20 may be coupled to shaft 16, for example, at a crimp band 22. Other connections are contemplated. In at least some instances, wire 20 may extend through sheath 12 to handle 14. Snare 18 may have an opening size (e.g., ID) of about 10 to 55 mm. Wire 20 may have a diameter of about 0.005-0.050 inches, or about 0.008-0.040 inches. The diameter of wire 20 may be chosen based on the length of snare. For example, a snare that is about 30 mm in length may utilize a wire having a diameter of about 0.025 inches. It should be noted that the diameter and/or shape of wire 20 may change along the length thereof as described in more detail herein.

Along snare 18, wire 20 may include a first end region 24a, a first loop region 26a, a first traction region 28a, a first distal region 30a, a distal end region or nipple region 32, a second distal region 30b, a second traction region 28b, a second loop region 26b, and a second end region 24b. The length and/or position of each region along snare 18 may vary. For example, in some instances first end region 24a and/or second end region 24b may extend in a direction that is substantially parallel to the longitudinal axis of sheath 12. First loop region 26a may extend from first end region 24a to first traction region 28a. First traction region 28a may begin at the first (e.g., the most proximal) of a plurality of traction members 34 disposed along snare 18. First distal region 30a may begin at the last (e.g., the most distal) traction member 34. Nipple region 32 may extend between first distal region 30a and second distal region 30b. In at least some instances, nipple region 32 projects distally to form the distal end of snare 18. Second traction region 28b may extend along traction members 34. Second loop region 26b may extend between second traction region 28b and second end region 24b. The regions can be understood to be regions of wire 20, regions of snare 18, or both.

Wire 20 may be thought of as defining two arms or legs of snare 18. In some instances, the two arms may be substantially the same. For example, first loop region 26a of a "first arm" of snare 18 may be substantially the same as second loop region 26b, and so on. In other instances, the arms may differ. For example, first traction region 28a may have a first length and a first number of traction members whereas second traction region 28b may have second length and a second number of traction members where the lengths, number of traction members, or both differ between arms. Other variations are contemplated for other regions of snare 18.

As indicated above, first traction region 28a, second traction region 28b, or both may include a plurality of traction members 34. The number of traction member 34 may vary. In some instances, first traction region 28a, second traction region 28b, or both may include 1, 2, 3, 4, 5, 6, 7, 8, 9, 10, or more traction members 34. Regions 28a/28b may have the same or a different number of traction members 34. The shape, form, spacing, and/or configuration of traction members 34 may vary. For example, in some instances traction members 34 may be oriented toward the interior of snare 18. Traction members 34 may be equally spaced along wire or may have a variable spacing (e.g., the density or number of traction members 34 per unit length can be equal or vary). Traction members 34 may have a pointed end, a square or rectangular end, or combinations thereof. The height of tractions member 34 can also vary. A number of additional variations for tractions members 34 are contemplated.

Figure 2:
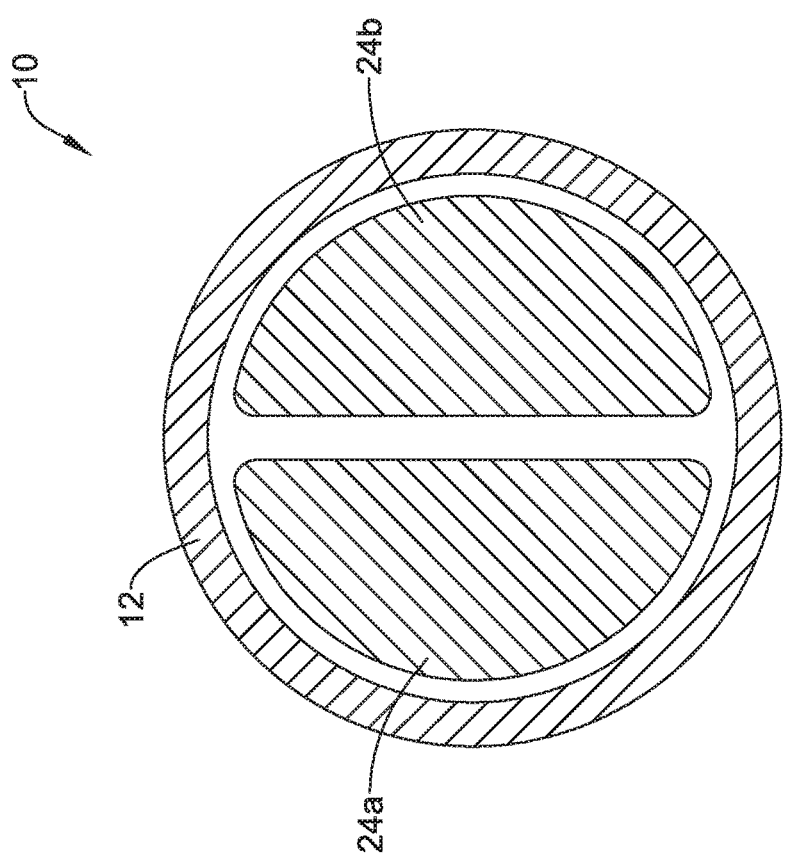
FIG. 2 is a cross-sectional view taken through line 2-2 in FIG. 1.
Figure 3:
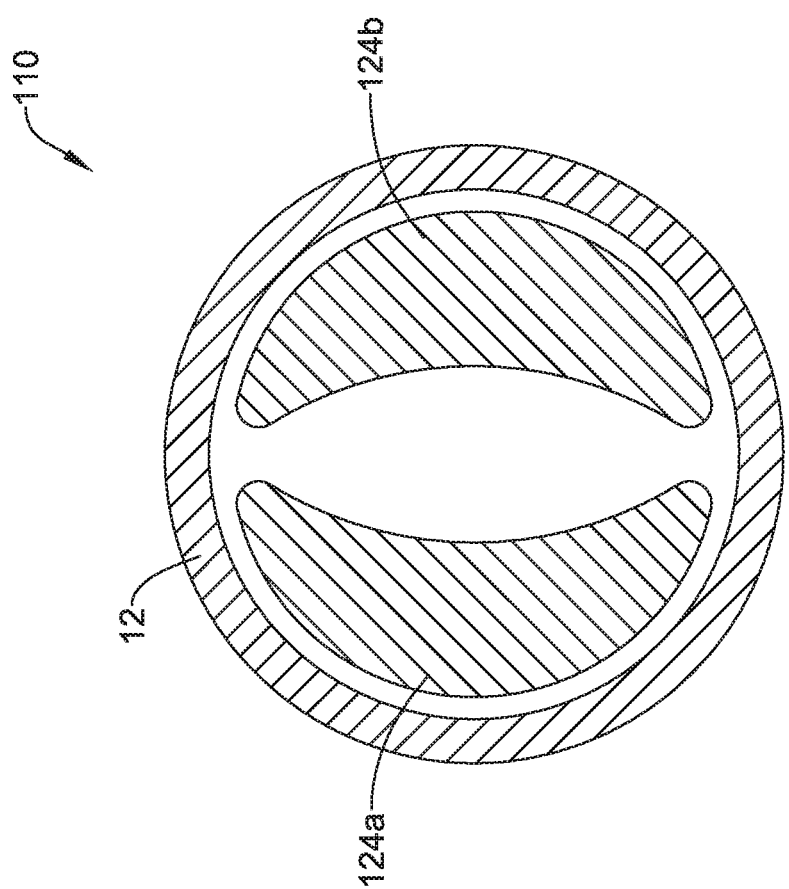
FIG. 3 is an alternative cross-sectional view.
Figure 4:
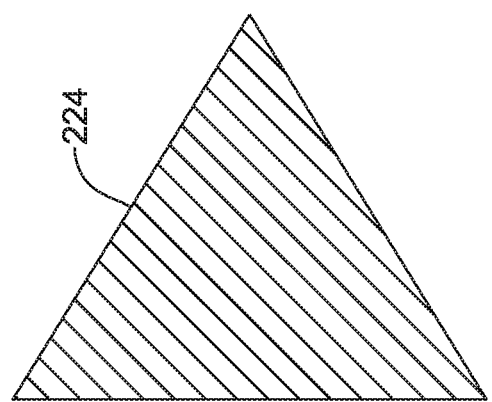
FIG. 4 is an alternative cross-sectional view.
Figure 5:
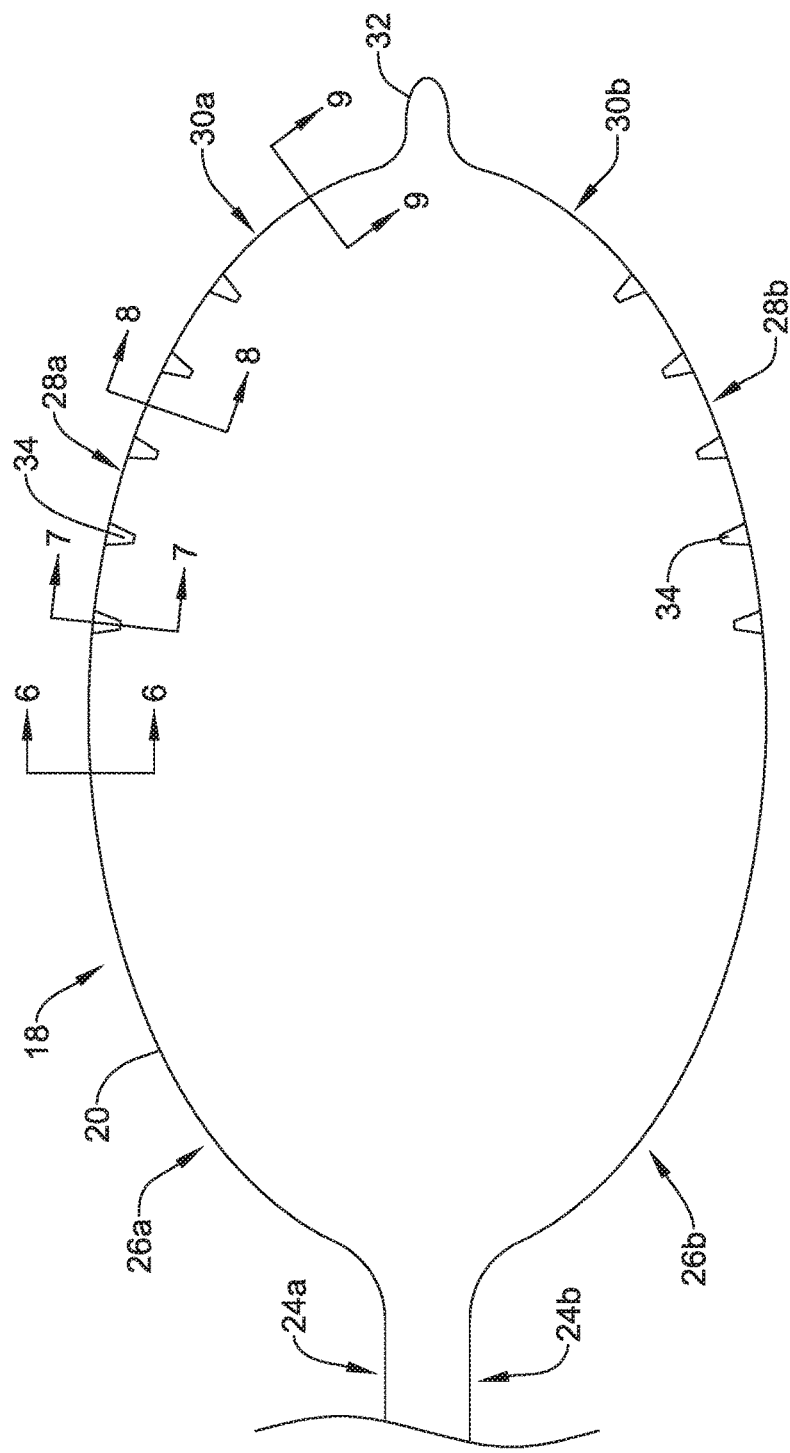
FIG. 5 is a top view of a portion of an example device.

In at least some instances, at least a portion of snare 18, wire 20 may have a non-circular cross-sectional shape. Furthermore, the cross-sectional shape and/or dimension of wire 20 may vary along snare 18. For example, FIG. 2 illustrates a portion of device 10 where it can be seen that first end region 24a and second end region 24b have a non-circular cross-sectional shape. In this instance, first end region 24a and second end region 24b have cross-sectional shape that is semi-circular or D-shaped. Other shapes are contemplated. For example, FIG. 3 illustrates a portion of device 110 where first end region 124a and second end region 124b are C-shaped. Other shapes are contemplated including L-shaped. In other instances, an end region (e.g., end region 224 as shown in FIG. 4) may have a polygonal cross-sectional shape such as a triangular shape, a tear-drop shape, an oval shape, or the like. Other shapes are contemplated.

Figure 6:
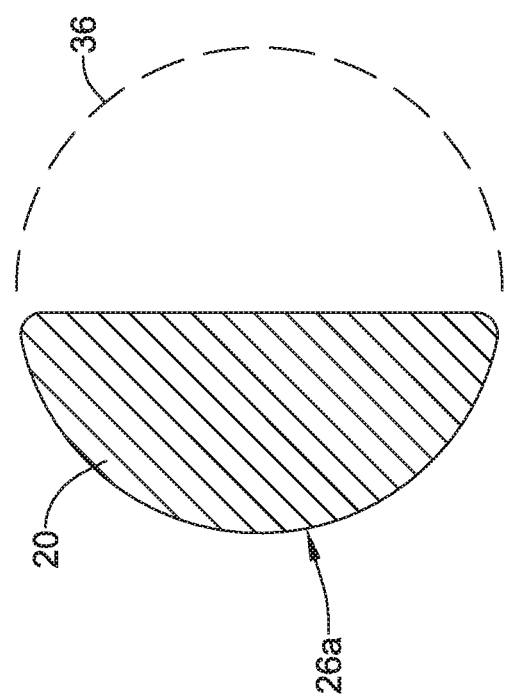
FIG. 6 is a cross-sectional view taken through line 6-6 in FIG. 5.

FIGS. 6-9 further illustrate how the shape, dimensions, and configuration of wire 20 may change along snare 18 (e.g., along the length of snare 18). For example, along first loop region 26a and/or second loop region 26b, wire 20 may have a non-circular cross-sectional shape such as a semi-circular or D-shape as depicted in FIG. 6. Such a shape may be the same or different from the cross-sectional shape of end regions 24a/24b. In at least some instances, the D-shaped of wire 20 is formed by grinding, electron discharge machining (EDM), laser cutting, stamping, precision electrolytic machining (PEM), milling, coining, another suitable mechanism, and/or machining a wire with a substantially round cross-sectional shape. For the purposes of this disclosure, any one or more of these processes (and/or other processes) may be understood to be "machining". In FIG. 6, reference number 36 is intended to show the perimeter of wire 20 prior to grinding. However, in other instances, the cross-sectional shape of loop regions 26a/26b may be formed by stamping. Other shapes are contemplated including L-shaped.

Figure 7:
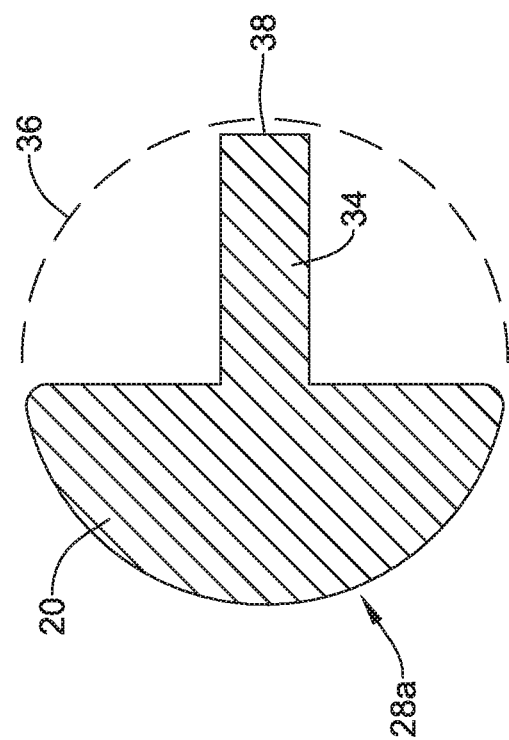
FIG. 7 is a cross-sectional view taken through line 7-7 in FIG. 5.

Wire 20 may also include a shape/size change in order to form traction members 34. For example, FIG. 7 illustrates that along first traction region 28a, wire 20 may include both a D-shaped portion and traction member 34 projecting therefrom. In some instances, traction member 34 may have a planar end region 38. Like the shape of wire 20 along first end region 24a and/or first loop region 26a, the shape of wire 20 illustrated in FIG. 7 may be formed by grinding or another suitable process.

Figure 8:
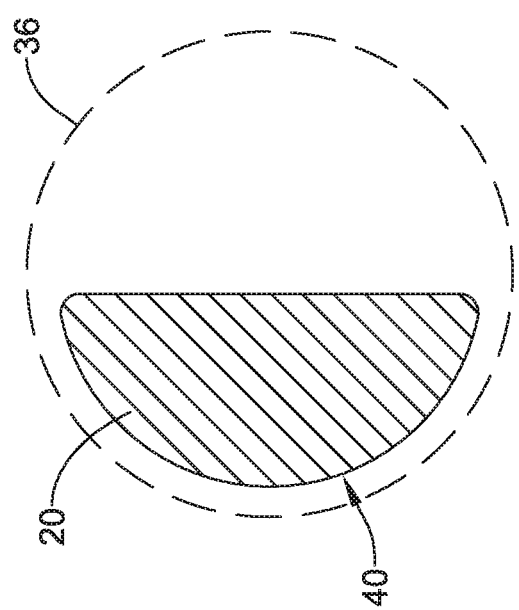
FIG. 8 is a cross-sectional view taken through line 8-8 in FIG. 5.

At a position along snare 18, the cross-sectional shape and/or size/dimensions of wire 20 may change. The transition in shape/size may occur at a number of different locations. For example, the shape/size of wire 20 may change along first loop region 26a, at the junction of first loop region 26a and first traction region 28a, along first traction region 28a, or along first distal region 30a. The transition may be gradual or more sudden/stepped. In some instances, at a location between adjacent traction members 34, wire 20 may further transition in shape and/or dimensions. For example, FIG. 8 illustrates that at a location 40 between two adjacent traction members 40, wire 20 may have a D-shaped cross-section. In this instance, the size of wire 20 is reduced relative to the perimeter 36 of wire 20 through grinding, EDM, or another suitable method. In other instances, wire 20 may be constant without a transition in size and/or shape.

Figure 9:
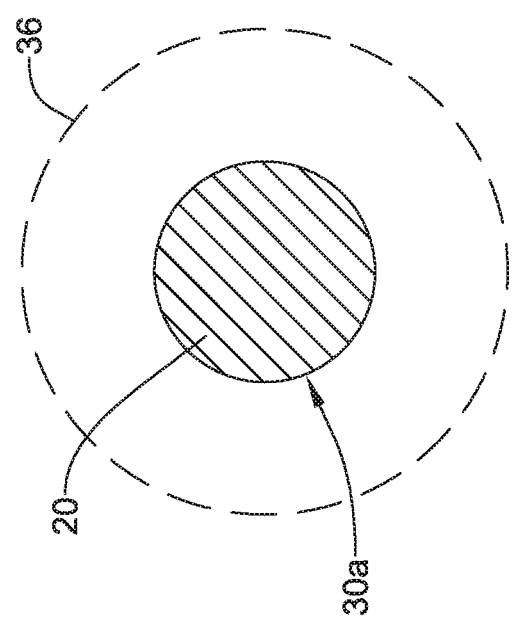
FIG. 9 is a cross-sectional view taken through line 9-9 in FIG. 5.

FIG. 9 illustrates that along first distal region 30a, wire 20 may have a substantially circular cross-sectional shape. The transition to a round cross-sectional shape may occur at the junction between first traction region 28a and first distal region 30a, at a position along first distal region 30a, at the junction between first distal region 30a and nipple region 32, etc. The round cross-sectional shape may extend through nipple region 32 to at least a portion of second distal region 30b. In at least some instances, nipple region 32 may have a diameter of about 0.005-0.025 inches, or about 0.009 inches. It may be desirable for nipple region 32 to be relatively short with a relatively wide base. This may aid in keeping snare 18 open during retraction of snare 18 into sheath 12. At some point along second distal region 30b, wire 20 may transition back to having a non-circular cross-section shape and further transition in a manner similar to the shape/sizes/transitions described above along first distal region 30a, first traction region 28a, and first end region 24a.

In use, device 10 may be navigated to a position adjacent to a target lesion (e.g., a sessile or flat lesion) or polyp. When suitably positioned, snare 18 (e.g., a monofilament snare 18) may be opened and the target lesion may be engaged by the traction members 34 (e.g., and/or the first traction region 28a and the second traction region 28b). Snare 18 may be at least partially retracted into sheath 12, which may at least partially close snare 18 and capture the lesion. In some instances, this may include applying a downward force with a portion of wire 20 such as, for example, first loop region 26a and/or second loop region 26b. The lesion may be cut with electrosurgical energy (e.g., application of electrocautery energy to wire 20) and/or by mechanical force applied by snare 18 (e.g., first distal region 30a and/or second distal region 30b).

Figure 10:
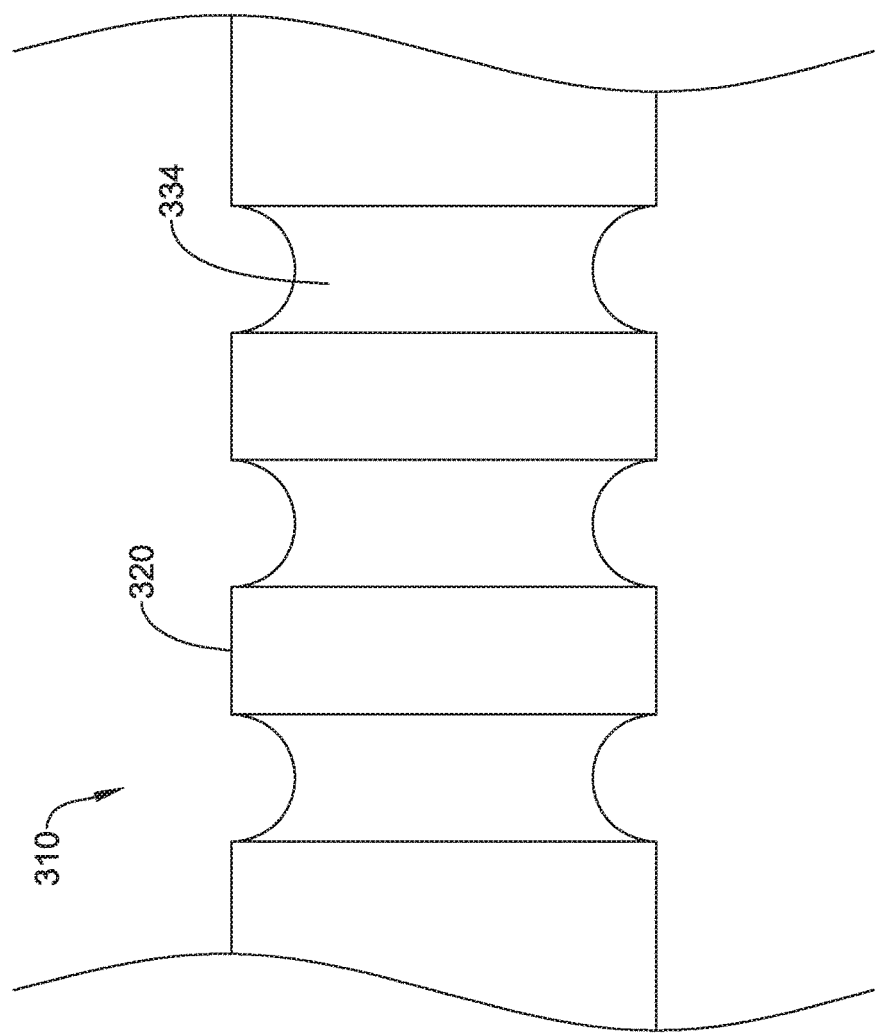
FIG. 10 is a side view of a portion of an example medical device.

FIG. 10 illustrates a portion of another example device 310 that may be similar in form and function to other devices disclosed herein. In this example, wire 320 may include a plurality of traction members 334 formed by annular grooves along wire 320. Grooves 334 may be formed by grinding or another suitable process. Grooves 334 may be disposed along a traction region of an example snare such as those snares disclosed herein.

Figure 11:
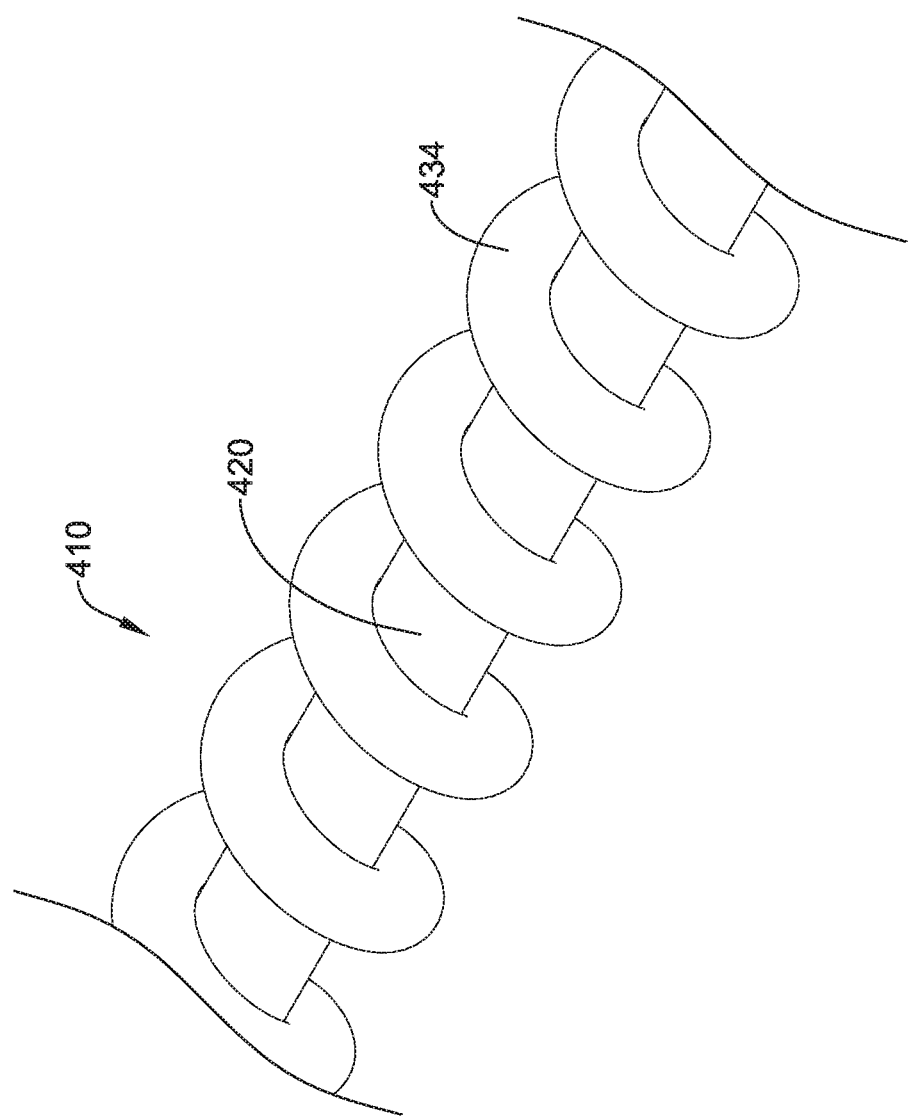
FIG. 11 is a perspective view of a portion of an example medical device.

FIG. 11 illustrates a portion of another example device 410 that may be similar in form and function to other devices disclosed herein. In this example, wire 420 may include helical traction members 434. Traction member 434 may be threaded onto or otherwise disposed along wire 420. Traction member 434 may be disposed along a traction region of an example snare such as those snares disclosed herein.

Figure 12:
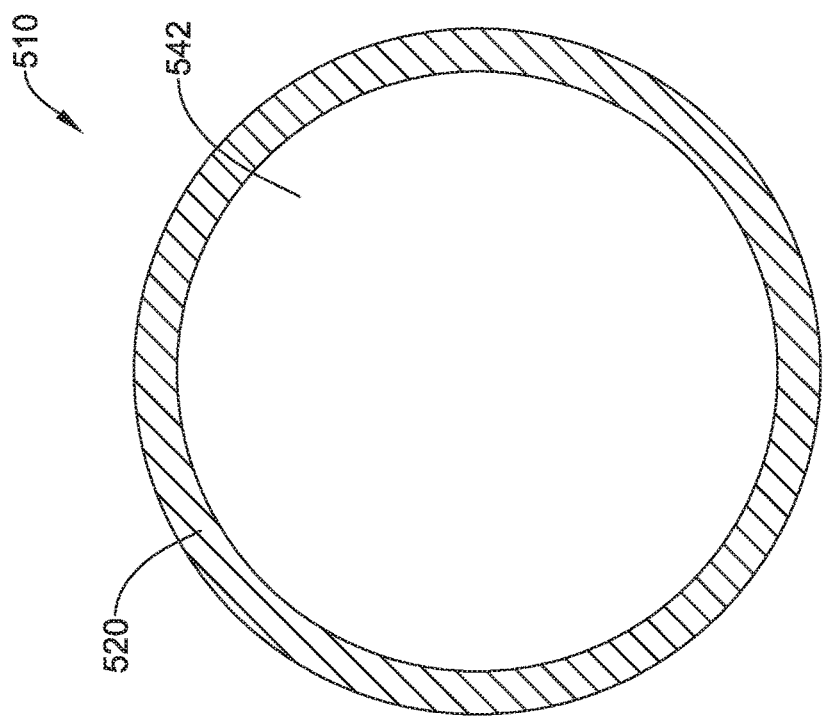
FIG. 12 is a cross-sectional view of a portion of an example medical device.
Figure 13:
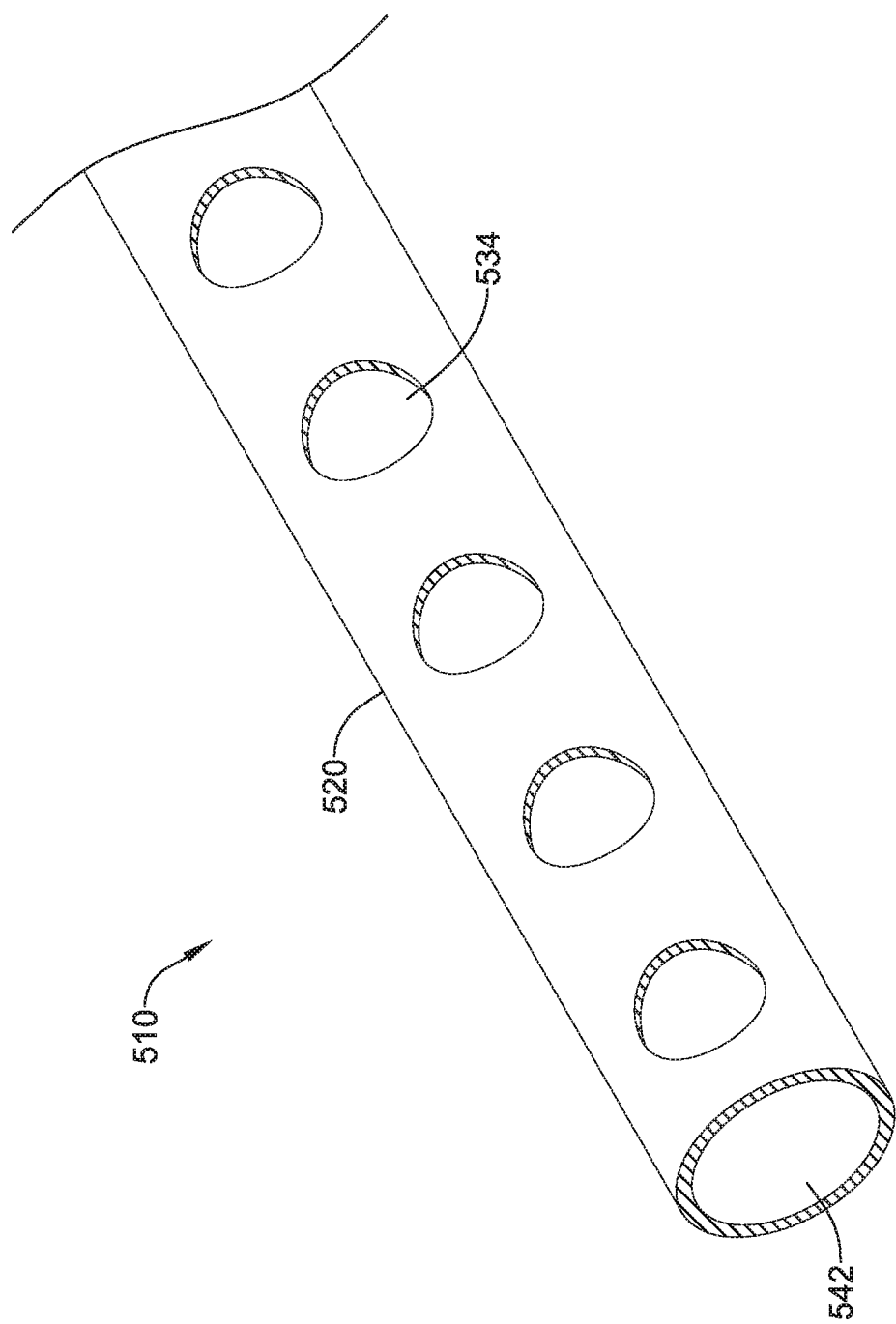
FIG. 13 is a partial cross-sectional view of a portion of an example medical device.

FIG. 12 illustrates a portion of another example device 510 that may be similar in form and function to other devices disclosed herein. In this example, a "tubular wire" or tube 520 may be utilized. Tube 520 may include a lumen 542. In some instances, one or more traction members 534 may be formed in tube 520 as side holes or apertures as shown in FIG. 13. Tube 520 may be used for example snares such as those snares disclosed herein. In some instances, tube 520 may be tapered or otherwise include one or more tapered sections (e.g., such as a distal tapered section).

Figure 14:
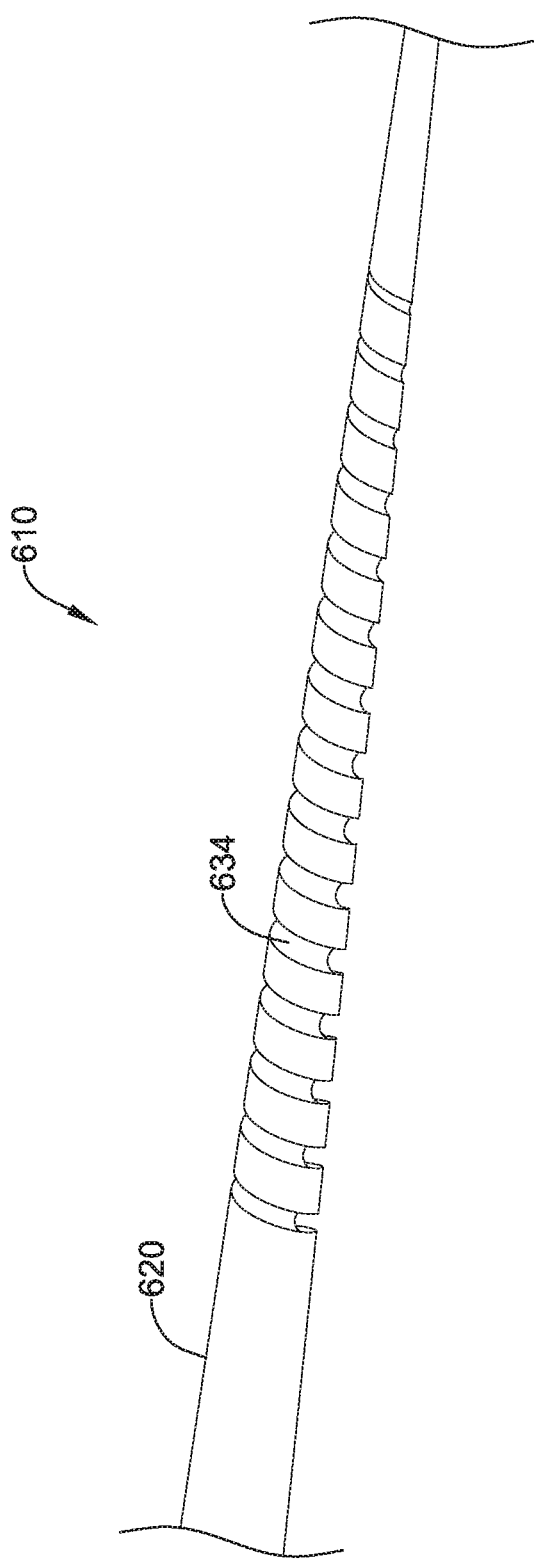
FIG. 14 is a side view of a portion of an example medical device.

FIG. 14 illustrates a portion of another example device 610 that may be similar in form and function to other devices disclosed herein. In this example, wire 620 may include a helical groove 634 formed therein. Helical groove 634 may form a plurality of traction members. In at least some instances, the pitch, depth, or both of helical groove 634 may vary along the length of wire 620. In addition, the shape and/or dimensions of wire 620 may also change.

The materials that can be used for the various components of polypectomy device 10 (and/or other polypectomy devices disclosed herein) and the various wires, snares, sheaths, etc. disclosed herein may include those commonly associated with medical devices. For simplicity purposes, the following discussion makes reference to sheath 12 and other components of device 10. However, this is not intended to limit the devices and methods described herein, as the discussion may be applied to other similar tubular members and/or components of the devices disclosed herein.

Sheath 12 and/or other components of device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of Magnetic Resonance Imaging (MRI) compatibility is imparted into device 10. For example, device 10, or portions thereof, may be made of a material that does not substantially distort the image and create substantial artifacts (e.g., gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A polypectomy device, comprising:
   an elongate sheath having a proximal end region and a distal end region;
   a shaft slidably disposed within the sheath;
   a handle coupled to the proximal end region of the sheath, the handle being designed to axially shift the shaft relative to the sheath;
   a snare coupled to the shaft, the snare including a first region, a traction region, and a distal tip region;
   wherein the first region has a first non-circular cross-sectional shape;
   wherein the traction region includes a plurality of traction members;
   wherein at a position between two adjacent traction members the snare has a second non-circular cross-sectional shape that is geometrically similar to the first non-circular cross-sectional shape and has a reduced cross-sectional area relative to the first region; and
   wherein the distal tip region has a circular cross-sectional shape.

2. The polypectomy device of claim 1, wherein the snare is formed from a monofilament wire.

3. The polypectomy device of claim 1, wherein the non-circular cross-sectional shape of the first region is D-shaped.

4. The polypectomy device of claim 3, wherein the snare has a first leg and a second leg, and wherein the non-circular cross-sectional shape of the first region is D-shaped along both the first leg and the second leg.

5. The polypectomy device of claim 3, wherein along the first region the first leg and the second leg are designed to be arranged so that planar sides of the first leg and the second leg are positioned adjacent to one another.

6. The polypectomy device of claim 1, wherein the non-circular cross-sectional shape of the first region is formed by machining a wire having a round cross-sectional shape.

7. The polypectomy device of claim 1, wherein at least some of the traction members have a first side having a rounded outer profile and a second side having a planar outer profile.

8. The polypectomy device of claim 1, wherein all of the plurality of traction members have geometrically congruent cross-sectional shapes.

9. The polypectomy device of claim 1, wherein at least some of the plurality of traction members have geometrically similar cross-sectional shapes.

10. The polypectomy device of claim 1, wherein the plurality of traction members are formed by a plurality of annular grooves formed along the snare.

11. The polypectomy device of claim 1, wherein the plurality of traction members are formed by a helical groove formed along the snare.

12. The polypectomy device of claim 11, wherein the helical groove varies in depth, pitch, or both along the length of the snare.

13. The polypectomy device of claim 1, wherein the plurality of traction members are formed by a helical member disposed along the snare.

14. The polypectomy device of claim 1, wherein the snare is formed from a tubular wire and wherein the plurality of traction members are defined by a plurality of apertures formed through a side wall of the tubular wire.

15. A polypectomy device, comprising:
    an elongate sheath;
    a shaft slidably disposed within the sheath;
    a monofilament snare wire coupled to the shaft, the snare wire having a first end region, a first loop region, a first traction region, a first distal region, a nipple region, a second distal region, a second traction region, a second loop region, and a second end region;
    wherein the first end region, the second end region, or both have a non-circular cross-sectional shape;
    wherein the first traction region, the second traction region, or both include a plurality of traction members;
    wherein the first distal region has a first reduced cross-sectional area relative to the first end region;
    wherein the second distal region has a second reduced cross-sectional area relative to the second end region;
    wherein at least one of the first distal region, the nipple region, and the second distal region has a circular cross-sectional shape; and
    wherein the first distal region has a first section having a non-circular cross-sectional shape, a second section having a circular cross-sectional shape, and a junction where the non-circular cross-sectional shape of the first section transitions to the circular cross-sectional shape of the second section.

16. The polypectomy device of claim 15, wherein the non-circular cross-sectional shape of the first end region, the second end region, or both is D-shaped.

17. The polypectomy device of claim 15, wherein at least some of the traction members have a first side with a rounded outer profile and a second side with a planar outer profile.

18. A method for manufacturing a polypectomy device, the method comprising:
- machining a monofilament wire to form a snare wire, the snare wire having a first end region, a first loop region, a first traction region, a first distal region, a nipple region, a second distal region, a second traction region, a second loop region, and a second end region;
- wherein the first end region, the second end region, or both have a non-circular cross-sectional shape;
- wherein the first traction region, the second traction region, or both include a plurality of traction members;
- wherein the first distal region has a first reduced cross-sectional area relative to the first end region;
- wherein the second distal region has a second reduced cross-sectional area relative to the second end region;
- wherein at least one of the first distal region, the nipple region, and the second distal region has a circular cross-sectional shape;
- wherein the first distal region has a first section having a non-circular cross-sectional shape and a second section having a circular cross-sectional shape;
- forming a junction along the first section where the non-circular cross-sectional shape of the first section transitions to the circular cross-sectional shape of the second section;
- attaching the first end region and the second end region to an elongate shaft; and
- disposing the elongate shaft within a sheath.

19. The method of claim 18, wherein the non-circular cross-sectional shape of the first end region, the second end region, or both is D-shaped.

20. The method of claim 18, wherein at least some of the traction members have a first side with a rounded outer profile and a second side with a planar outer profile.

* * * * *